United States Patent
Heggendorn et al.

(10) Patent No.: US 9,662,217 B2
(45) Date of Patent: May 30, 2017

(54) FEMORAL KNEE PROSTHESIS WITH DIVERGING LATERAL CONDYLE

(71) Applicant: ZIMMER GMBH, Winterthur (CH)

(72) Inventors: Marco A. H. Heggendorn, Pura (CH); Matthias Schäpper, Winterthur (CH); Roger Scherrer, Schlatt (CH)

(73) Assignee: Zimmer GmbH, Winterthur (CH)

( * ) Notice: Subject to any disclaimer, the term of this patent is extended or adjusted under 35 U.S.C. 154(b) by 0 days.

(21) Appl. No.: 14/509,753

(22) Filed: Oct. 8, 2014

(65) Prior Publication Data
US 2015/0025644 A1 Jan. 22, 2015

Related U.S. Application Data

(63) Continuation of application No. 14/131,986, filed as application No. PCT/EP2012/063575 on Jul. 11, 2012, now abandoned.
(Continued)

(51) Int. Cl.
*A61F 2/38* (2006.01)

(52) U.S. Cl.
CPC .............. *A61F 2/3836* (2013.01); *A61F 2/38* (2013.01); *A61F 2/3859* (2013.01); *A61F 2002/3863* (2013.01); *A61F 2250/0073* (2013.01)

(58) Field of Classification Search
CPC ........ A61F 2/38; A61F 2/3868; A61F 2/3886; A61F 2/3859
(Continued)

(56) References Cited

U.S. PATENT DOCUMENTS

| 3,798,679 A | 3/1974 | Ewald |
| 3,816,855 A | 6/1974 | Saleh |

(Continued)

FOREIGN PATENT DOCUMENTS

| EP | 0123016 A1 | 10/1984 |
| EP | 1121074 B1 | 7/2008 |

(Continued)

OTHER PUBLICATIONS

"U.S. Appl. No. 12/692,371, Response filed Jan. 26, 2012 to Non Final Office Action mailed Oct. 26, 2011", 12 pgs.
(Continued)

*Primary Examiner* — Alvin Stewart
(74) *Attorney, Agent, or Firm* — Schwegman Lundberg & Woessner, P.A.

(57) ABSTRACT

A knee prosthesis has a femoral component with a medial condyle defining a constant bearing spacing relative to a central sagittal component plane SP, and a lateral condyle defining divergent bearing spacing from the central sagittal component plane along an extension-to-flexion path. High congruence between the medial articulation surfaces creates a pivot point for external rotation at the medial contact area, while lower congruence in the lateral articulation surfaces allows the lateral femoral condyle to track anteriorly and posteriorly during flexion. The amount of lateral condyle bearing spacing divergence is calculated to produce a substantially linear anteroposterior motion profile of the lateral femoral condyle upon the lateral tibia articular surface throughout a wide range of flexion.

13 Claims, 8 Drawing Sheets

Related U.S. Application Data (60) Provisional application No. 61/507,413, filed on Jul. 13, 2011.

(58) Field of Classification Search
USPC ......... 623/20.21, 20.26, 20.27, 20.31, 20.35, 623/20.24
See application file for complete search history.

(56) References Cited

U.S. PATENT DOCUMENTS

| | | | |
|---|---|---|---|
| 4,112,522 A | 9/1978 | Dadurian et al. | |
| 4,209,861 A | 7/1980 | Walker et al. | |
| 4,215,439 A | 8/1980 | Gold | |
| 5,147,405 A | 9/1992 | Van Zile | |
| 5,219,362 A * | 6/1993 | Tuke | A61F 2/38 623/20.31 |
| 5,282,870 A * | 2/1994 | Moser | A61F 2/38 623/20.31 |
| 5,330,534 A | 7/1994 | Herrington et al. | |
| 5,358,527 A | 10/1994 | Forte | |
| 5,370,699 A | 12/1994 | Hood et al. | |
| 5,413,604 A * | 5/1995 | Hodge | A61F 2/3868 623/20.28 |
| 5,549,686 A * | 8/1996 | Johnson | A61F 2/3886 623/20.27 |
| 5,728,162 A | 3/1998 | Eckhoff | |
| 6,013,103 A * | 1/2000 | Kaufman | A61F 2/38 623/20.15 |
| 6,056,779 A * | 5/2000 | Noyer | A61F 2/38 623/20.32 |
| 6,342,075 B1 | 1/2002 | MacArthur | |
| 6,406,497 B2 | 6/2002 | Takei et al. | |
| 6,475,241 B2 | 11/2002 | Pappas | |
| 6,491,726 B2 | 12/2002 | Pappas | |
| 6,558,426 B1 | 5/2003 | Masini | |
| 6,660,039 B1 | 12/2003 | Evans et al. | |
| 6,699,291 B1 | 3/2004 | Augoyard et al. | |
| 6,764,516 B2 | 7/2004 | Pappas | |
| 6,783,550 B2 | 8/2004 | MacArthur | |
| 6,797,005 B2 | 9/2004 | Pappas | |
| 7,081,137 B1 * | 7/2006 | Servidio | A61F 2/3886 623/20.14 |
| 7,160,330 B2 | 1/2007 | Axelson, Jr. et al. | |
| 7,309,362 B2 | 12/2007 | Yasuda et al. | |
| 7,326,252 B2 | 2/2008 | Otto et al. | |
| 7,351,263 B2 | 4/2008 | Afriat | |
| 7,413,577 B1 | 8/2008 | Servidio | |
| 7,615,054 B1 | 11/2009 | Bonutti | |
| 7,635,390 B1 | 12/2009 | Bonutti | |
| 8,192,498 B2 | 6/2012 | Wagner et al. | |
| 8,236,061 B2 | 8/2012 | Heldreth et al. | |
| 8,491,661 B2 * | 7/2013 | Mouillet | A61F 2/3886 623/20.21 |
| 8,932,365 B2 * | 1/2015 | Parisi | A61F 2/3859 623/20.27 |
| 9,132,014 B2 | 9/2015 | Sanford et al. | |
| 2003/0009232 A1 | 1/2003 | Metzger et al. | |
| 2004/0143339 A1 * | 7/2004 | Axelson, Jr. | A61F 2/3886 623/20.21 |
| 2005/0209701 A1 * | 9/2005 | Suguro | A61F 2/3886 623/20.27 |
| 2007/0135925 A1 | 6/2007 | Walker | |
| 2007/0135926 A1 * | 6/2007 | Walker | A61F 2/3859 623/20.31 |
| 2007/0173946 A1 | 7/2007 | Bonutti | |
| 2007/0233269 A1 | 10/2007 | Steines et al. | |
| 2008/0097615 A1 | 4/2008 | Lipman et al. | |
| 2008/0119940 A1 | 5/2008 | Otto et al. | |
| 2009/0210066 A1 | 8/2009 | Jasty | |
| 2009/0222103 A1 * | 9/2009 | Fitz | A61F 2/30942 623/18.11 |
| 2009/0306786 A1 * | 12/2009 | Samuelson | A61B 17/155 623/20.31 |
| 2009/0319047 A1 * | 12/2009 | Walker | A61F 2/3886 623/20.15 |
| 2009/0319049 A1 * | 12/2009 | Shah | A61F 2/38 623/20.31 |
| 2009/0326665 A1 * | 12/2009 | Wyss | A61F 2/3868 623/20.21 |
| 2010/0016977 A1 | 1/2010 | Masini | |
| 2010/0016979 A1 * | 1/2010 | Wyss | A61F 2/3886 623/20.27 |
| 2010/0036499 A1 * | 2/2010 | Pinskerova | A61F 2/38 623/20.31 |
| 2010/0042224 A1 | 2/2010 | Otto et al. | |
| 2010/0161067 A1 * | 6/2010 | Saleh | A61F 2/38 623/20.31 |
| 2010/0249940 A1 | 9/2010 | Sanford | |
| 2010/0305708 A1 | 12/2010 | Lang | |
| 2010/0329530 A1 | 12/2010 | Lang et al. | |
| 2011/0144760 A1 | 6/2011 | Wong et al. | |
| 2012/0089234 A1 * | 4/2012 | Mouillet | A61F 2/3886 623/20.21 |
| 2012/0095563 A1 * | 4/2012 | Sanford | A61F 2/38 623/20.27 |
| 2012/0095564 A1 * | 4/2012 | Mihalko | A61F 2/38 623/20.27 |
| 2012/0179265 A1 * | 7/2012 | Wyss | A61F 2/38 623/20.14 |
| 2012/0323337 A1 * | 12/2012 | Parisi | A61F 2/3886 623/20.35 |
| 2013/0006373 A1 * | 1/2013 | Wyss | A61F 2/3886 623/20.27 |
| 2013/0190884 A1 * | 7/2013 | Hashida | A61F 2/3836 623/20.29 |
| 2013/0197653 A1 * | 8/2013 | Hawkins | A61F 2/3886 623/20.27 |
| 2013/0204380 A1 * | 8/2013 | Mouillet | A61F 2/3886 623/20.27 |
| 2014/0243989 A1 * | 8/2014 | Nabeshima | A61F 2/3886 623/20.27 |
| 2015/0134067 A1 * | 5/2015 | Qu | A61F 2/3836 623/20.24 |
| 2015/0164646 A1 * | 6/2015 | Muratoglu | A61F 2/3886 623/20.27 |
| 2015/0305873 A1 | 10/2015 | Sanford et al. | |

FOREIGN PATENT DOCUMENTS

| | | |
|---|---|---|
| EP | 1555962 B1 | 2/2011 |
| EP | 2324799 A2 | 5/2011 |
| EP | 2335654 A1 | 6/2011 |
| JP | 2004166802 A | 6/2004 |
| WO | WO-0023011 A1 | 4/2000 |
| WO | WO-2005051240 A1 | 6/2005 |
| WO | WO-2006058057 A2 | 6/2006 |
| WO | WO-2007109641 A2 | 9/2007 |
| WO | WO-2011018441 A1 | 2/2011 |
| WO | WO-2011072235 A2 | 6/2011 |
| WO | WO-2012031774 A1 | 3/2012 |
| WO | WO-2012112698 A2 | 8/2012 |
| WO | WO-2013007747 A1 | 1/2013 |

OTHER PUBLICATIONS

"U.S. Appl. No. 12/692,371, Response filed May 11, 2012 to Non Final Office Action mailed Oct. 26, 2011", 3 pgs.

"U.S. Appl. No. 12/692,371, Response filed Aug. 26, 2011 to Restriction Requirement mailed Jul. 7, 2011", 2 pgs.

"U.S. Appl. No. 12/692,371, Response filed Feb. 25, 2014 to Final Office Action dated Sep. 25, 2013", 15 pgs.

"U.S. Appl. No. 13/086,104, Response filed Feb. 19, 2013, to Non Final Office Action mailed Oct. 18, 2012", 16 pgs.

"U.S. Appl. No. 13/086,104, Response filed Jul. 9, 2013 to Final Office Action mailed Apr. 9, 2013", 13 pgs.

"U.S. Appl. No. 13/086,104, Response filed Oct. 1, 2012 to Restriction Requirement mailed Aug. 29, 2012", 6 pgs.

"International Application Serial No. PCT/EP2012/063575, Written Opinion mailed Oct. 11, 2012 ", 7 pgs.

(56) References Cited

OTHER PUBLICATIONS

"U.S. Appl. No. 12/692,371, Non Final Office Action mailed Apr. 9, 2015", 8 pgs.
"U.S. Appl. No. 12/692,371, Response filed Jun. 16, 2015 to Non-Final Office Action mailed Apr. 9, 2015", 17 pgs.
"U.S. Appl. No. 13/086,104, Advisory Action mailed Apr. 1, 2015", 3 pgs.
"U.S. Appl. No. 13/086,104, Final Office Action mailed Jan. 27, 2015", 12 pgs.
"U.S. Appl. No. 13/086,104, Notice of Allowance mailed May 1, 2015", 5 pgs.
"U.S. Appl. No. 13/086,104, Response filed May 26, 2015 to Final Office Action mailed Jan. 27, 2015", 16 pgs.
"U.S. Appl. No. 13/086,104, Response filed Apr. 21, 2015 to Advisory Action mailed Apr. 1, 2015", 16 pgs.
"U.S. Appl. No. 13/086,104, Response filed Nov. 24, 2014 to Non Final Office Action mailed May 28, 2014", 15 pgs.
"U.S. Appl. No. 14/131,986, Preliminary Amendment filed Jan. 10, 2014", 3 pgs.
"U.S. Appl. No. 12/692,371, Response filed Jan. 20, 2016 to Non-Final Office Action mailed Oct. 20, 2015", 16 pgs.
"U.S. Appl. No. 14/793,152, Preliminary Amendment filed Jul. 7, 2015", 3 pgs.
"U.S. Appl. No. 14/793,152, Supplemental Preliminary Amendment filed Jul. 9, 2015", 8 pgs.
"U.S. Appl. No. 14/826,807, Non Final Office Action mailed Oct. 20, 2015", 9 pgs.
U.S. Appl. No. 14/793,152, filed Jul. 7, 2015, Anterior Cruciate Ligament Substituting Knee Implants.
U.S. Appl. No. 13/086,104, filed Apr. 13, 2011, Anterior Cruciate Ligament Substituting Knee Implants.
U.S. Appl. No. 14/131,986, filed Jan. 10, 2014, Femoral Knee Prosthesis With Diverging Lateral Condyle.
U.S. Appl. No. 12/692,371, filed Jan. 22, 2010, Posterior-Stabilized Total Knee.
"U.S. Appl. No. 12/692,371, Examiner Interview Summary mailed Apr. 8, 2013", 3 pgs.
"U.S. Appl. No. 12/692,371, Final Office Action mailed Sep. 25, 2013", 9 pgs.
"U.S. Appl. No. 12/692,371, Non Final Office Action mailed Oct. 26, 2011", 8 pgs.
"U.S. Appl. No. 12/692,371, filed Jan. 26, 2012 to Non Final Office Action mailed Oct. 26, 2011", 12 pgs.
"U.S. Appl. No. 12/692,371, filed May 11, 2012 to Non Final Office Action mailed Oct. 26, 2011", 3 pgs.
"U.S. Appl. No. 12/692,371, filed Aug. 26, 2011 to Restriction Requirement mailed Jul. 7, 2011", 2 pgs.
"U.S. Appl. No. 12/692,371, filed Feb. 25, 2014 to Final Office Action dated Sep. 25, 2013", 15 pgs.
"U.S. Appl. No. 12/692,371, Restriction Requirement mailed Jul. 7, 2011", 6 pgs.
"U.S. Appl. No. 13/086,104, Final Office Action mailed Apr. 9, 2013", 8 pgs.
"U.S. Appl. No. 13/086,104, Non Final Office Action mailed May 28, 2014", 15 pgs.
"U.S. Appl. No. 13/086,104, Non Final Office Action mailed Oct. 18, 2012", 12 pgs.
"U.S. Appl. No. 13/086,104, filed Feb. 19, 2013 to Non Final Office Action mailed Oct. 18, 2012", 16 pgs.
"U.S. Appl. No. 13/086,104, filed Jul. 9, 2013 to Final Office Action mailed Apr. 9, 2013", 13 pgs.
"U.S. Appl. No. 13/086,104, filed Oct. 1, 2012 to Restriction Requirement mailed Aug. 29, 2012", 6 pgs.
"U.S. Appl. No. 13/086,104, Restriction Requirement mailed Aug. 29, 2012", 6 pgs.
"U.S. Appl. No. 61/381,803, filed Sep. 10, 2010", 23 pgs.
"Bi-Cruciate Stabilized Knee System", Design Rationale, Smith & Nephew Journal, (2006), 20 pgs.
"Complete Knee Solution Surgical Technique for the CR-Flex Fixed Bearing Knee", Zimmer Nexgen, (2003), 22 pgs.
"International Application Serial No. PCT/EP2012/063575, Demand and Letter filed May 13, 2013", 11 pgs.
"International Application Serial No. PCT/EP2012/063575, International Preliminary Report on Patentability mailed Dec. 2, 2013", 9 pgs.
"International Application Serial No. PCT/EP2012/063575, International Search Report mailed Oct. 11, 2012", 5 pgs.
"International Application Serial No. PCT/EP2012/063575, Written Opinion mailed Oct. 11, 2012", 7 pgs.
"International Application Serial No. PCT/US2010/021818, International Preliminary Report on Patentability mailed Jul. 26, 2011", 8 pgs.
"International Application Serial No. PCT/US2010/021818, International Search Report mailed Apr. 20, 2010", 4 pgs.
"International Application Serial No. PCT/US2010/021818, Written Opinion mailed Apr. 20, 2010", 8 pgs.
"LPS Flex Fixed Bearing Knee", Zimmer Surgical Technique, (2004, 2007), 12 pgs.
Li, Guoan, et al., "Anterior Cruciate Ligament Deficiency Alters the In Vivo Motion of the Tibiofemoral Cartilage Contact Points in Both the Anteroposterior and Mediolateral Directions", The Journal of Bone & Joint Surgery, (2006), 1826-1834.
"U.S. Appl. No. 12/692,371, Notice of Allowance mailed Dec. 5, 2016", 7 pgs.

* cited by examiner

FEMORAL KNEE PROSTHESIS WITH DIVERGING LATERAL CONDYLE

CLAIM OF PRIORITY

This application is a continuation of U.S. patent application Ser. No. 14/131,986, filed on Jan. 10, 2014, which is a U.S. National Stage Application based on International Application Serial No. PCT/EP2012/063575, filed on Jul. 11, 2012, published on Jan. 17, 2013 as WO2013/007747 A1, which claims the benefit of U.S. Provisional Patent Application Ser. No. 61/507,413, filed on Jul. 13, 2011, the benefit of priority of each of which is claimed hereby, and each of which are incorporated by reference herein in its entirety.

BACKGROUND

1. Technical Field

The present disclosure relates to orthopaedic prostheses, and more particularly, to femoral prosthetic components with enhanced tibia femoral articulation characteristics.

2. Description of the Related Art

Orthopaedic prostheses are commonly utilized to repair and/or replace damaged bone and tissue in the human body. For example, a knee prosthesis may be used to repair damaged or diseased articular surfaces of the femur and/or tibia to restore natural function. A knee prosthesis may include a femoral component which replaces the articular surfaces of one or both of the natural femoral condyles, and/or the natural femoral sulcus. The femoral component typically articulates with a tibial component which replaces the proximal articular surface of the tibia.

A goal of knee replacement procedures is to reproduce natural knee kinematics using the associated prosthetic components. More generally such procedures seek to achieve kinematic characteristics that promote favorable patient outcomes including minimized pain, short recovery time, minimized risk of joint subluxation, and a long service life of the prosthesis components.

For example, a prosthetic knee may accommodate or induce "rollback" of the lateral femoral condyle in deep flexion, thereby replicating the rollback phenomenon experienced by a natural knee. Femoral rollback results from the natural tendency of the tibia and femur to rotate relative to one another, about their longitudinal axes, as the knee progresses from extension to deep flexion. This rotation process is referred to as "external rotation" because the anterior surface of the femur rotates externally or away from the center of the patient. Corresponding internal rotation of the femur accompanies lateral femoral "roll-forward" as the knee is articulated back toward extension.

External rotation and femoral rollback are a function of differential congruency between the medial and lateral articular surfaces of the knee. In particular, a normal natural knee has a high congruence between the medial femoral condyle and the corresponding medial tibial articular surface, but a lower congruence between the lateral femoral condyle and tibial articular surface. This differential congruency cooperates with interacting forces exerted by the soft tissues of the knee joint, including the posterior cruciate ligament (PCL), anterior cruciate ligament (ACL), medial and lateral cruciate ligaments (MCL and LCL), and the associated leg muscles linking the knee ligaments to the tibia or femur.

Previous design efforts have focused on providing prosthetic components which facilitate and/or accommodate femoral rollback and external rotation of the knee, particularly at medium and deep levels of knee flexion.

U.S. Pat. No. 5,219,362 to Tuke et al. discloses a knee prosthesis which permits internal/external rotation. The Tuke prosthesis has an asymmetric femoral component 1 with a medial condyle 3 (FIG. 1) that is larger than the lateral condyle 4. The medial condyle 3 has a surface portion which is largely spherical and is shaped to be substantially congruent with a spherical concave depression 6, while the lateral condyle 4 forms an incongruent contact with a trough-shaped depression 7 in the tibial component 2. The lateral depression 7, shown in FIG. 4, forms an arc shaped curve in plan view, with the curve having as its center the center point 9 of medial depression 6. The trough-shaped lateral depression 7 permits relative rotation between the tibia and femur about the axis through center point 9.

International PCT Application No. PCT/GB99/03407 to Walker discloses a femoral prosthesis which interacts with a corresponding tibial component to promote posterior displacement of the femoral component during flexion, and anterior displacement during extension. The Walker prosthesis utilizes a gradually changing frontal profile of the femoral condylar bearing surfaces from the distal to the posterior region and a corresponding intercondylar hump to achieve divergence of contact points between the femoral and tibial components from anterior to posterior, as shown in FIG. 2. For example, at zero degrees flexion as shown in FIG. 3(a), the distance separating contact points 11L and 11M is indicated as dimension X. At 60° flexion as shown in FIG. 3(b), the contact points 12L and 12M are separated by a distance 'y' which is greater than distance 'x'. At maximum flexion of 120° as shown in FIG. 3(c), the contact points 13L and 13M are still further separated by a distance Z. The divergence of the femoral condyles creates an intercondylar groove which becomes deeper at higher levels of flexion, and the intercondylar hump formed on the tibial surface has a correspondingly increasing height from anterior to posterior (FIGS. 4(a)-4(c). The rise of the hump is steepest approaching the posterior side, which has the effect of assisting a roll forward movement as the femoral component rolls down the hump during extension.

SUMMARY

The present disclosure provides a knee prosthesis in which the femoral component has a medial condyle defining a constant bearing spacing relative to a central sagittal component plane, and a lateral condyle defining divergent bearing spacing from the central sagittal component plane along an extension-to-flexion path. High congruence between the medial articulation surfaces creates a pivot point for external rotation at the medial contact area, while lower congruence in the lateral articulation surfaces allows the lateral femoral condyle to track anteriorly and posteriorly during flexion. The amount of lateral condyle bearing spacing divergence is calculated to produce a substantially linear anteroposterior motion profile of the lateral femoral condyle upon the lateral tibia articular surface throughout a wide range of flexion.

Advantageously this linear anteroposterior articulation profile accommodates and facilitates rollback of the lateral condyle arising from external rotation of the femoral component in deep flexion, and thereby ensures consistent, large-area contact between the articular surfaces of the femoral and tibial component throughout a wide flexion range.

In one form thereof, the present disclosure provides a femoral component for a knee prosthesis, the femoral component comprising: a medial condyle having a convex medial articular surface defining: a medial distal-most point, and an arcuate medial condylar track extending posteriorly along the medial articular surface from the medial distal-most point, the arcuate medial condylar track defining a medial radius of articulation; and a lateral condyle having a convex lateral articular surface defining: a lateral distal-most point, and an arcuate lateral condylar track extending posteriorly along the lateral articular surface from the lateral distal-most point, the arcuate lateral condylar track defining a lateral radius of articulation, the femoral component defining: an articulation axis passing through the medial radius of articulation and the lateral radius of articulation, a transverse plane tangent to at least one of the lateral distal-most point and the medial distal-most point, a coronal plane perpendicular to the transverse plane, parallel to the articulation axis, and tangent to at least one of the medial articular surface and the lateral articular surface, and a sagittal plane perpendicular to the transverse plane and the coronal plane, the sagittal plane mediolaterally positioned to bisect the articulation axis, the arcuate medial condylar track defining a constant condylar spacing from the sagittal plane, and the arcuate lateral condylar track defining a divergent condylar spacing from the sagittal plane as the lateral condylar track extends posteriorly.

In another form thereof, the present disclosure provides a knee prosthesis comprising: a femoral component having a convex medial femoral condyle and a convex lateral femoral condyle; and a tibial bearing component having a medial articular surface adapted to articulate with the medial femoral condyle through a range of flexion, and a lateral articular surface adapted to articulate with the lateral femoral condyle through the range of flexion, the medial femoral condyle defining a plurality of medial femoral contact points with the medial articular surface at a plurality of flexion levels within the range of flexion, each of the medial femoral contact points disposed at a substantially constant spatial position on the medial articular surface, the lateral femoral condyle defining a plurality of lateral femoral contact points with the lateral articular surface at the plurality of flexion levels, each of the lateral femoral contact points disposed along a substantially linear path on the lateral articular surface.

In yet another form thereof, the present disclosure provides a knee prosthesis comprising: a femoral component having a convex medial femoral condyle and a convex lateral femoral condyle; and a tibial bearing component having a medial articular surface adapted to articulate with the medial femoral condyle through a range of flexion, and a lateral articular surface adapted to articulate with the lateral femoral condyle through the range of flexion, the medial femoral condyle contacting a medial point on the medial articular surface at a first degree of flexion, the medial femoral condyle maintaining contact with the medial point at a second degree of flexion, the lateral femoral condyle contacting a lateral point on the lateral articular surface at the first degree of flexion, the lateral femoral condyle losing contact with the lateral point at the second degree of flexion, the lateral femoral condyle experiencing rollback along a substantially linear path from the first degree of flexion to the second degree of flexion.

BRIEF DESCRIPTION OF THE DRAWINGS

The above-mentioned and other features and advantages of this disclosure, and the manner of attaining them, will become more apparent and the invention itself will be better understood by reference to the following description of embodiments of the invention taken in conjunction with the accompanying drawings, wherein.

Corresponding reference characters indicate corresponding parts throughout the several views. The exemplifications set out herein illustrate exemplary embodiments of the invention, and such exemplifications are not to be construed as limiting the scope of the invention in any manner.

DETAILED DESCRIPTION

Figure 1A:
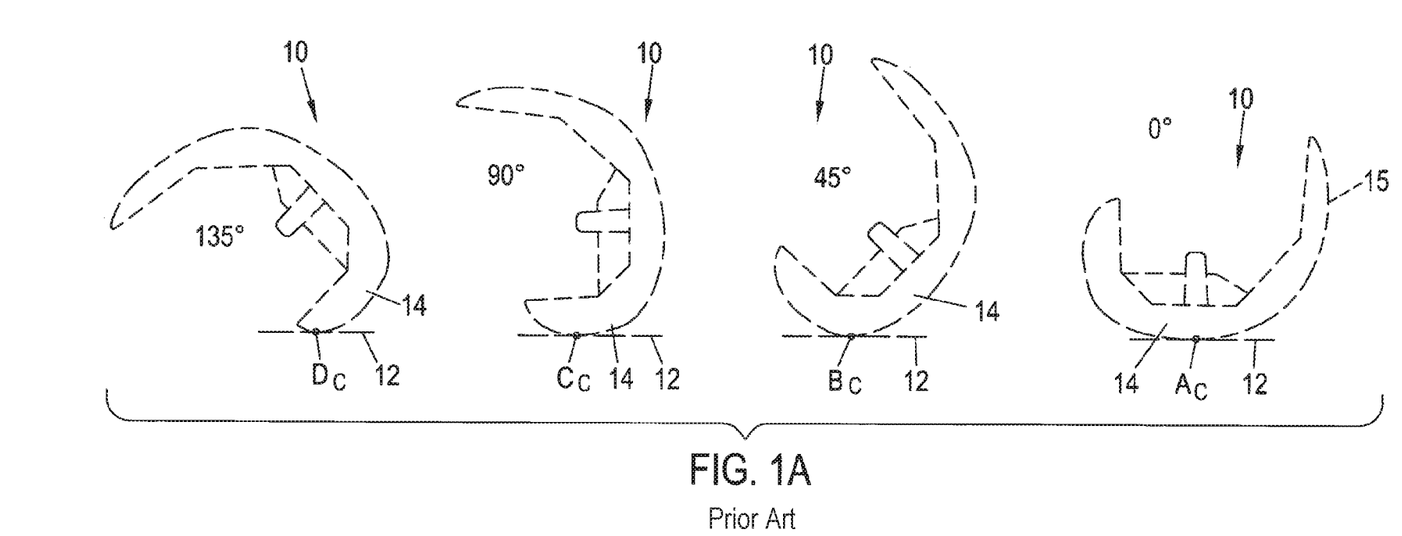
FIG. 1A is a collection of elevation views of a femoral component, illustrating the component in four different rotational orientations.

Turning to FIG. 1A, one type of femoral component 10 is shown from a sagittal viewpoint, with component 10 resting on flat surface 12. When component 10 is oriented in a position corresponding to zero degrees flexion, as shown on the right side of FIG. 1A, component 10 defines contact point $A_C$ between flat surface 12 and the distal-most point on the articular surface of lateral femoral condyle 14. As component 10 is rolled along flat surface 12 to position corresponding to about 45° flexion, femoral component 10 defines contact point $B_C$ between lateral condyle 14 and flat surface 12. Similarly, as femoral component 10 is rolled further upon flat surface 12 to positions corresponding to 90° flexion and 135° flexion, contact points $C_C$ and $D_C$ are respectively defined between respective posterior portions of condyle 14 and flat surface 12.

Applicants refer to contact "points" herein in the context of contact between femoral and tibial components. While it is appreciated that such contact actually creates a contact area comprised of many contact points, for purposes of the present discussion a "contact point" may be said to be the point at the geometric center of a the area of contact.

Figure 1B:
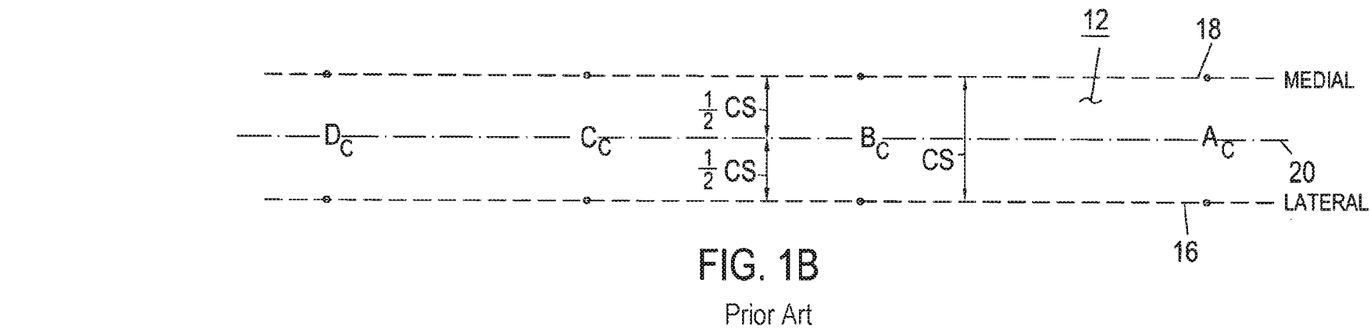
FIG. 1B is a schematic plan view illustrating constant bearing spacing of the femoral component of FIG. 1A across the different rotational orientations.

FIG. 1B illustrates that femoral component 10 has constant "bearing spacing" between condyles 14, 15 throughout the various levels of flexion. In particular, FIG. 1B illustrates a tracing of the paths created by lateral condyle 14 and the medial condyle 15 upon flat surface 12 as femoral component 10 is rotated as described above. Both track 16 of lateral condyle 14 and track 18 of medial condyle 15 define a consistent condylar spacing CS at and between contact points $A_C$, $B_C$, $C_C$, and $D_C$. Further, lateral condyle 14 and the medial condyle are generally symmetrical about central sagittal plane 20, such that the distance between both lateral condylar track 16 and medial condylar track 18 defines a distance equal to one-half of condylar spacing CS between sagittal plane 20 and lateral and medial condylar tracks 16, 18.

Figure 1C:
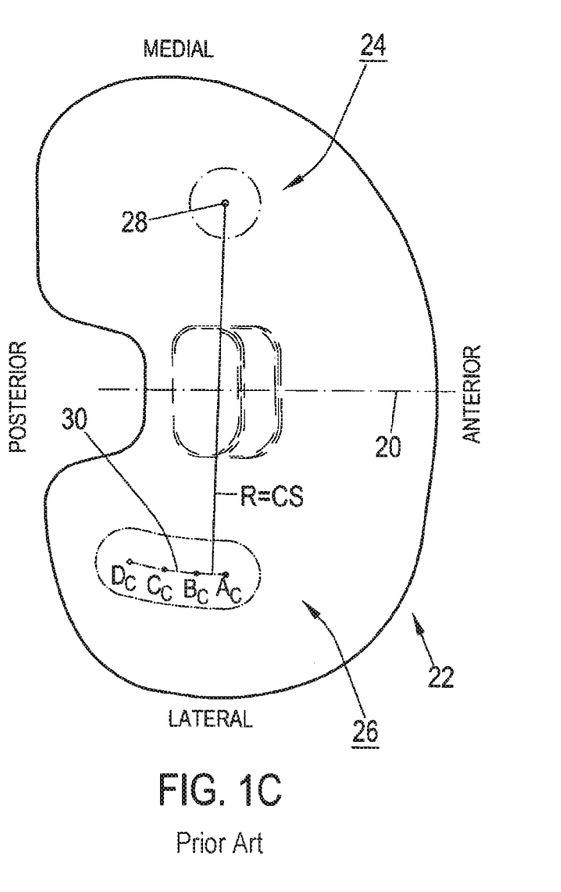
FIG. 1C is a top plan view of a tibial bearing component, illustrating an arcuate articulation path of the femoral component of FIG. 1A on the tibial bearing component.

When femoral component 10 is paired with tibial component 22 (FIG. 1C), the character of articulation of lateral and medial femoral condyles 14, 15 changes as compared to rolling femoral component 10 upon a flat surface. Similarly to the knee prosthesis disclosed in U.S. Pat. No. 5,219,362 to Tuke et al. (discussed above), medial tibial articular surface 24 may be shaped to have a high congruence with medial condyle 15, while lateral tibial articulate surface 26 may be shaped to have a lower congruence with lateral condyle 14. Referring to FIG. 1C, the high congruence therebetween between medial condyle 15 and medial articular surface 24 keeps contact point 28 substantially stationary during articulation of femoral component 10 with tibial component 22.

On the other hand, the lower congruence between lateral condyle 14 and lateral articular surface 26 combines with constant condylar spacing CS to produce contact points $A_C$, $B_C$, $C_C$, and $D_C$ defining arcuate path 30. More particularly, as posterior rollback of lateral condyle 14 occurs along arcuate path 30 because constant condylar spacing CS gives rise to a correspondingly constant radius R throughout articulation of femoral component 10 upon tibial component 22. Medial contact point 28 forms the center about which lateral condyle 14 externally rotates, creating lateral arcuate path 30.

The present disclosure provides a femoral component for a knee prosthesis in which the bearing spacing of the lateral condyle diverges with respect to a sagittal plane along an extension-to-flexion path, while the corresponding bearing spacing of the medial condyle remains constant with respect to the sagittal plane.

As the femoral component articulates with respect to the tibial component during flexion of the knee, high congruence between the medial femoral condyle and medial tibial articular surface keeps the medial tibial/femoral contact point in a substantially constant spatial position, thereby creating a pivot point for internal/external rotation of the femoral component. Lower congruence between the lateral femoral condyle and lateral tibial articular surface allows lateral femoral rollback to occur as the femur externally rotates during deep flexion, such that the lateral tibial/femoral contact point tracks posteriorly. The divergence of the lateral condyle from the sagittal plane is calculated to compensate for external rotation, such that the lateral femoral/tibial contact point tracks in a linear, anteroposterior fashion. Such linear tracking maintains a constant tibiofemoral congruence when the lateral tibial bearing surface defines a substantially straight anteroposterior depression.

Figure 2A:
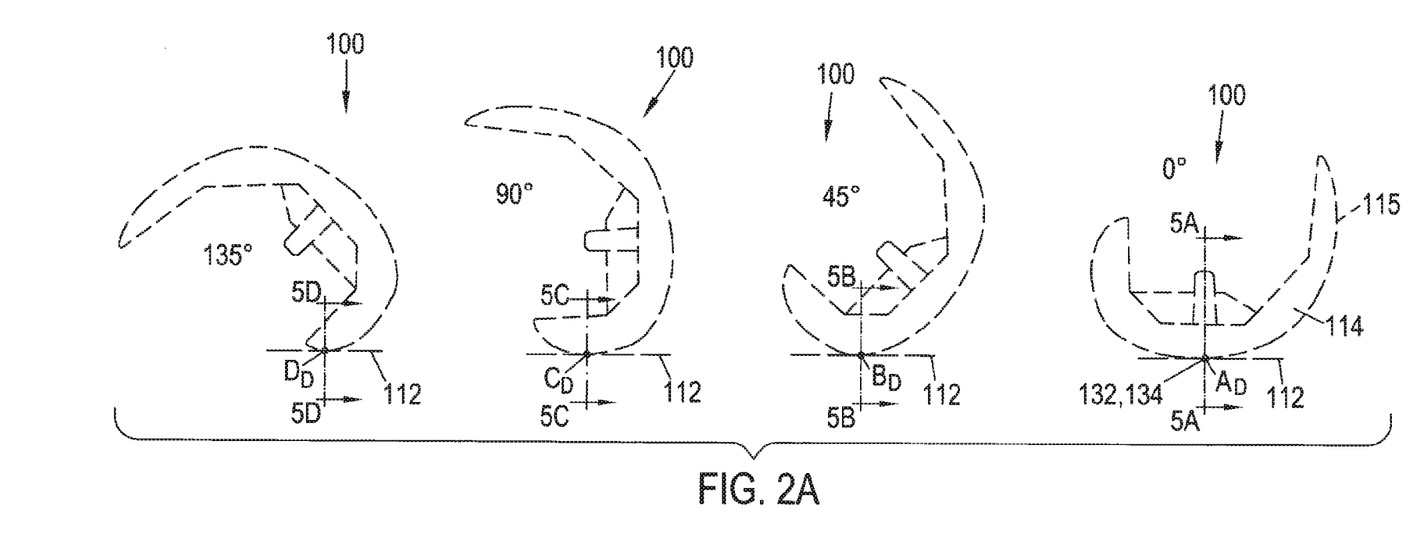
FIG. 2A is a collection of elevation views of a femoral component in accordance with the present disclosure, illustrating the component in four different rotational orientations.

Referring now to FIG. 2A, femoral component 100 is shown resting upon flat surface 112 four different rotational orientations. When femoral component 100 is in a rotational orientation corresponding to full extension of a knee (i.e., zero degrees flexion), the distal-most points 132, 134 of lateral and medial condyles 114, 115 (see also FIG. 4) define contact points $A_D$ with flat surface 112. As femoral component 100 is rolled along flat surface 112 to a rotational orientation corresponding to 45° flexion (FIG. 2A, second from right), lateral and medial condyles 114, 115 define contact points $B_D$ on flat surface 112. Similarly, rolling femoral component 100 further to a rotational orientation corresponding to 90° flexion produces contact points $C_D$, and rolling femoral component 100 to a rotational orientation corresponding to 135° flexion produces contact points $D_D$.

Figure 2B:
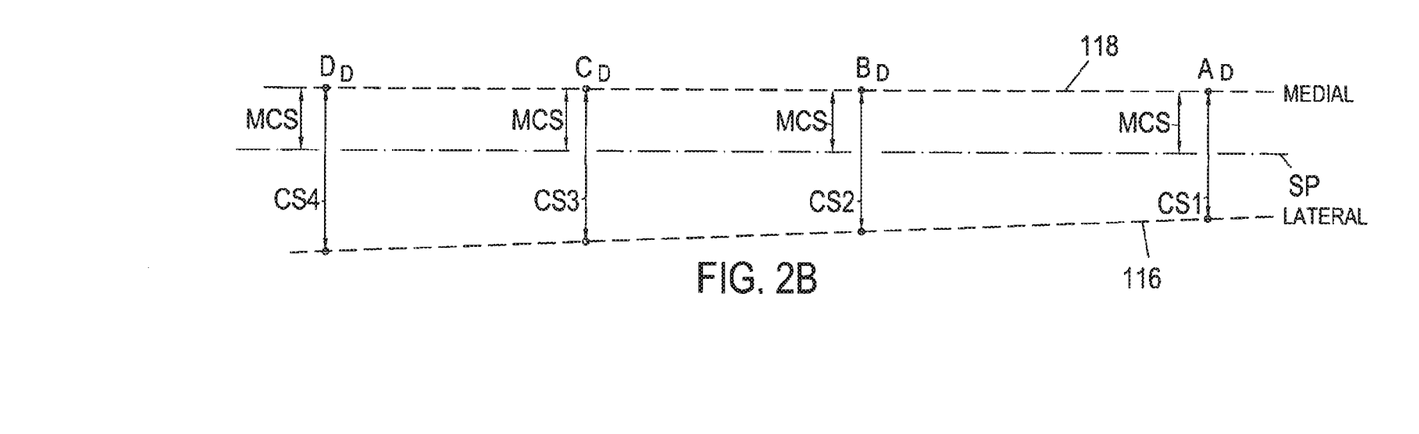
FIG. 2B is a schematic plan view illustrating laterally-divergent bearing spacing of the femoral component of FIG. 2A across the different rotational orientations.
Figure 3A:
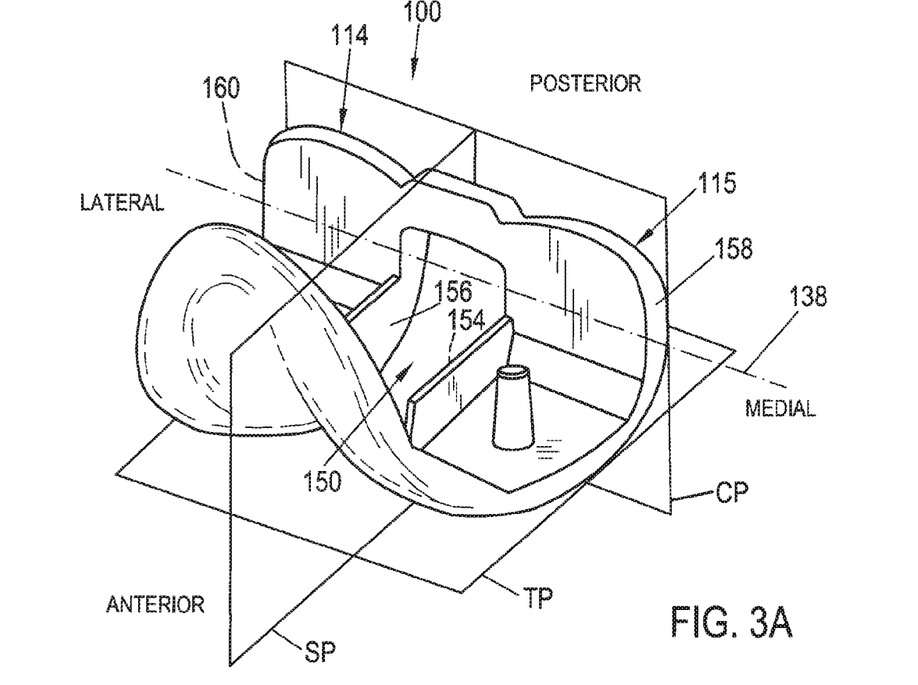
FIG. 3A is a perspective view of a femoral component made in accordance with the present disclosure, illustrating component coordinate planes.

FIG. 2B illustrates schematic plan view of lateral and medial condylar tracks 116, 118 (see also FIG. 4) produced by rolling femoral component 100 on flat surface 112 as described above and shown in FIG. 2A. Contact points $A_D$ define a condylar bearing spacing CS1 between tracks 116, 118. The distance from medial track 118 to a central sagittal plane SP (component planes are also shown in FIG. 3A, and discussed in detail below) of femoral component 100 is illustrated as medial condylar spacing MCS.

In the second-from-right view of FIGS. 2A and 2B, femoral component 100 has been rotated by 45° upon flat surface 112. In this new configuration, lateral and medial contact points 162,164 (FIG. 4) of lateral and medial condyles 114, 115 define condylar bearing spacing CS2 at contact points $B_D$. Condylar spacing CS2 is larger than condylar spacing CS1, but medial condylar spacing MCS remains unchanged because divergence of the lateral condylar track 116 accounts for all of the additional condylar spacing gained between 0° and 45° rotation.

In the second-from left view of FIGS. 2A and 2B, femoral component 100 has been further rotated to a rotational orientation corresponding to 90° flexion. Lateral and medial contact points 166,168 (FIG. 4) of lateral and medial condyles 114, 115 define condylar bearing spacing CS3 at contact points $C_D$, with condylar spacing CS3 larger than condylar spacing CS2. Medial condylar spacing MCS remains unchanged, with the additional condylar spacing again being entirely accounted for by the divergence of lateral condylar track 116 from sagittal plane SP.

Similarly, a rotational orientation of 135° results in condylar spacing CS4 at contact points $D_D$, with condylar spacing CS4 larger than condylar spacing CS3. Medial condylar spacing MCS again remains unchanged, and lateral condylar track 116 has diverged still further from sagittal plane SP.

Thus, femoral component 100 defines divergent condylar spacing CS1, CS2, CS3, CS4 between the contact points of lateral and medial condyles 114, 115, with the minimum spacing at distal-most points 132, 134 of condyles 114, 115 and increasing spacing at condylar points corresponding to increasingly deeper flexion of the knee. Divergent condylar spacing CS1, CS2, CS3, CS4 arises entirely from divergence of the lateral condyle 114 from a central sagittal plane SP of femoral component 100, whereas medial condyle 115 does not contribute to the condylar divergence.

Figure 2C:
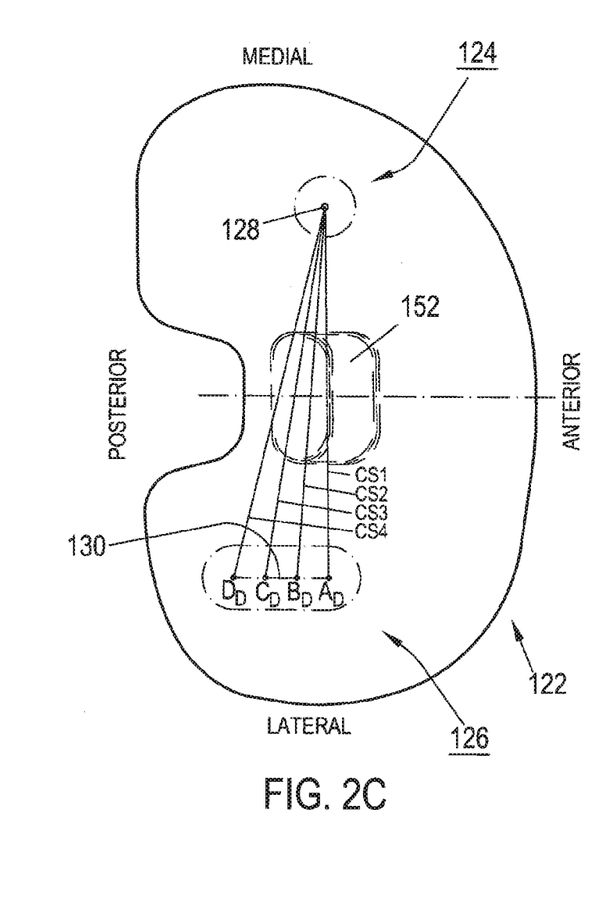
FIG. 2C is a top plan view of a tibial bearing component in accordance with the present disclosure, illustrating a substantially straight articulation path of the femoral component of FIG. 2A on the tibial bearing component.

Turning to FIG. 2C, a top plan view of tibial component 122 illustrates the substantially linear anteroposterior path 130 of articulation defined by contact points $A_D$, $B_D$, $C_D$, and $D_D$ as femoral component 100 is articulated upon medial and lateral tibial articular surfaces 124, 126. The amount of increase in condylar spacing CS1, CS2, CS3 and CS4 is calculated to offset relative medial movement of the contact point between lateral condyle 114 and lateral tibial articular surface 126, which would otherwise result from external rotation and femoral rollback (as shown in FIG. 1C). Where condylar spacing is calculated to produce such an offset throughout the range of knee motion, linear path 130 is produced.

Thus, although the lateral condylar spacing is schematically shown in FIG. 2B as having a constant rate of increase (illustrated by the linearity of lateral condylar track 116), it is contemplated that the increase may occur in a non-constant fashion as required for a particular design. Moreover, femoral components in accordance with the present disclosure may have a lateral condyle which diverges by any amount, with any rate of change of divergence across the articular range of motion, in order to compensate for the femoral rollback and external rotation inherent to any particular knee prosthesis design.

Coordinate System of the Femoral Component

Referring now to FIG. 3A, femoral component 100 defines three perpendicular coordinate planes: sagittal plane SP, transverse plane TP, and coronal plane CP. For purposes of the present disclosure, each of coordinate planes SP, TP, CP are referenced to femoral component 100, rather than to the anatomical planes defined by the human body. In the anatomical context (e.g., when femoral component 100 is implanted), coordinate planes SP, TP, CP may also be referenced to femur F (FIG. 3C) and are therefore fixed in their respective orientations and positions relative to femoral component 100 and femur F. Thus, coordinate planes SP, TP, CP move with femur F, and are not impacted by movements in other parts of a patient's body.

Given that sagittal plane SP, transverse plane TP, and coronal plane CP are indexed to femur F when femoral component 100 is implanted, it follows that planes SP, TP, CP generally correspond to sagittal, transverse, and coronal planes of the entire human body when the knee is in a fully extended orientation. However, planes SP, TP, CP are not necessarily co-planar or parallel with these human-body anatomic planes when the knee is not fully extended.

In one exemplary embodiment, transverse plane TP is defined as a plane tangent to distal-most points 132, 134 of lateral and medial condyles 114, 115 respectively. Generally speaking, the "distal-most points" of a femoral component of a knee prosthesis are those points which make the distal-most contact with the corresponding tibial bearing component when the knee prosthesis is in a full extension orientation.

Figure 4:
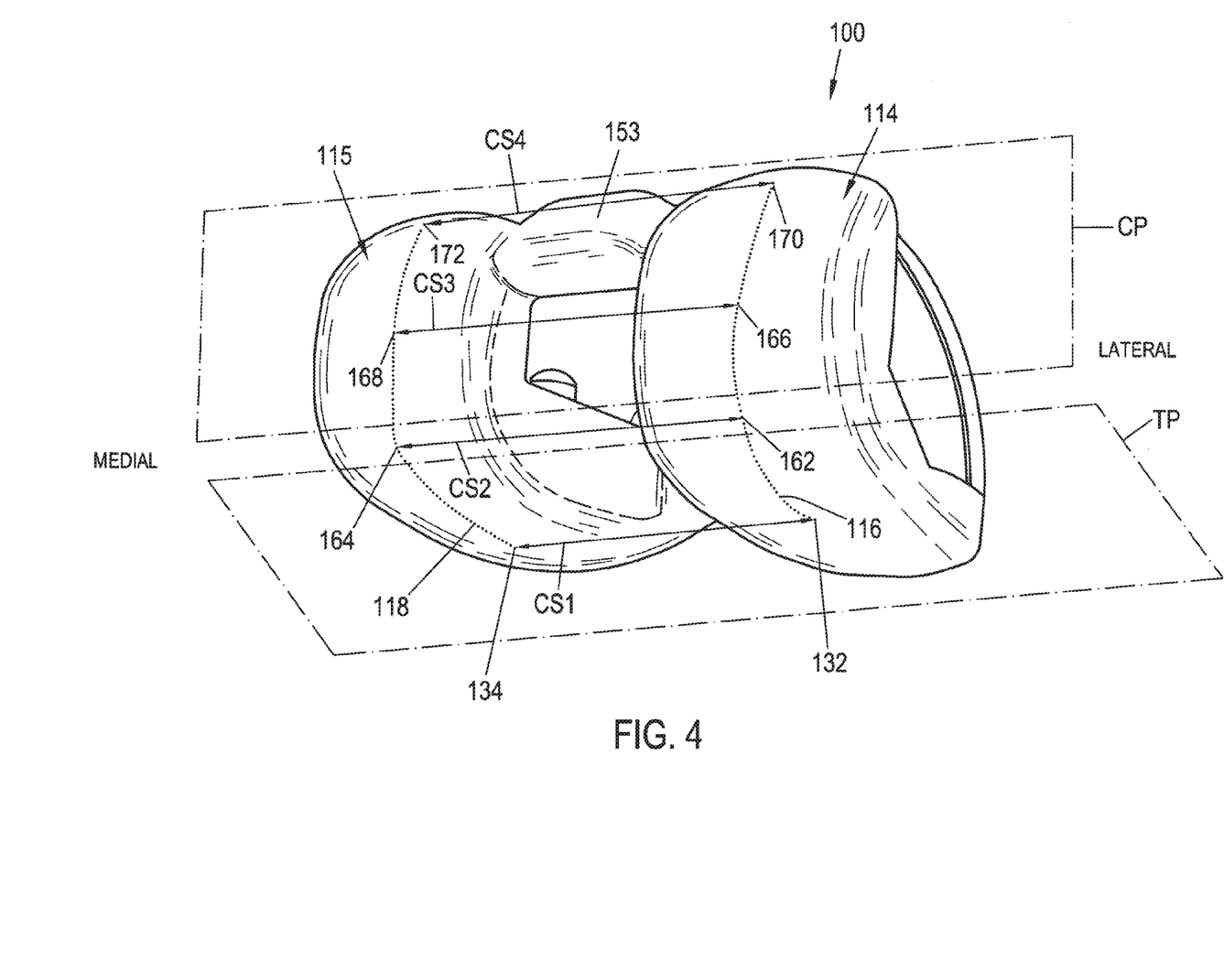
FIG. 4 is another perspective view of the femoral component shown in FIG. 3A, illustrating a changing condylar spacing from distal to posterior condylar articulating surfaces.

In the illustrative embodiment of FIG. 4, lateral and medial condyles 114, 115 each define bearing surfaces that are three-dimensionally convex at distal-most points 132, 134. Stated another way, the lateral and medial bearing surfaces have no flat surfaces at distal-most points 132, 134. Recognizing that a three-dimensionally convex surface can define only one tangent plane at a particular point, transverse plane TP may be defined as tangent to one or both of distal-most points 132, 134 depending on the particular geometrical configuration of condyles 114, 115. For many femoral components, transverse planes tangent to distal-most points 132, 134, are coplanar or nearly coplanar, such that a selection of either of distal-most points 132, 134 is suitable to form the basis of a component-based coordinate system.

Figure 3B:
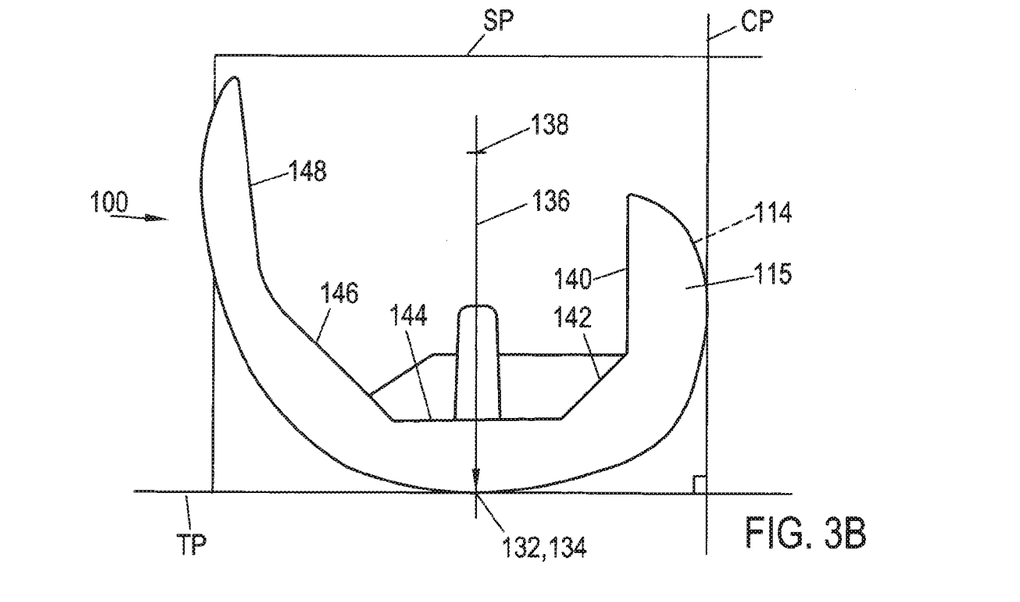
FIG. 3B is a sagittal, elevation view of the femoral component shown in FIG. 3A.

In the exemplary embodiment of FIGS. 3A and 3B, coronal plane CP is defined by three constraints. First, coronal plane CP is perpendicular to transverse plane TP (discussed above). Second, coronal plane CP is tangent to the posterior articular surface of one or both of lateral and medial condyles 114, 115. Third, coronal plane CP is parallel to articulation axis 138 (FIGS. 3A and 3B), which is the axis about which femoral component 100 rotates during articulation with tibial bearing component 122 (FIG. 5A) from full extension. In the context of femoral component 100 alone, articulation axis 138 is formed by connecting the origins of radii taken from the "J-curve" of the medial and lateral condyles at the distal-most points 132, 134 thereof. For example, as shown in FIG. 3B, medial condyle 115 defines a J-shaped arcuate profile in a sagittal, elevation view of component 100. This arcuate profile defines articulation radius 136 at distal-most point 134. A corresponding radius of articulation is formed at distal-most point 132 of lateral condyle 114. Articulation axis 138 passes through each of these two radii.

Referring still to the exemplary embodiment of FIGS. 3A and 3B, sagittal plane SP is also defined by three constraints. First, sagittal plane SP is perpendicular to transverse plane TP. Second, sagittal plane SP is perpendicular to coronal plane CP. Third, sagittal plane SP "bisects" femoral component 100. Generally speaking, sagittal plane SP may be said to bisect a line connecting distal-most points 132, 134 (see, for example, condylar spacing CS1 of FIG. 4), such that sagittal plane SP is equidistant from distal-most points 132, 134. Alternatively, sagittal plane SP may bisect articulation axis 138, such that sagittal plane SP is equidistant from the origins of the sagittal radii which define articulation axis 138.

Practically speaking, femoral components are sold with a particular surgical procedure envisioned for component implantation. Depending on the particular geometry and accompanying surgical procedure, a person having ordinary skill in the art of orthopaedic prostheses will be able to define "distal-most points" of a femoral prosthesis component and coordinate planes SP, TP, CP in accordance with the present disclosure.

In the illustrative femoral component 100 shown in FIG. 3B, for example, femoral component 100 is implanted by making a "box cut" at the distal end of femur F (FIG. 3C) to create a five-faceted resected bone surface sized to accept component 100. FIG. 3D shows a knee joint from a sagittal viewpoint, and illustrates various bone cuts that may be made to align implant components. Distal femoral cut 50 is typically made perpendicular to a projection of femoral axes AA, MA (further described below) in the sagittal plane. Proximal tibial cut 52 is typically made to match the natural posterior slope 54 of the proximal portion of tibia T relative to horizontal plane 56 which is perpendicular to mechanical axis MA. The distance between distal femoral cut 50 and proximal tibial cut 52 along mechanical axis MA may be referred to as the "extension gap." The distal femur and proximal tibia are typically resected to be parallel to joint line 58 (FIG. 3C), and thus perpendicular to mechanical axis MA, as projected in coronal plane CP and indicated at 50 and 52.

Other cuts may be made depending on the components that are to be implanted. These include anterior femoral cut 60, anterior femoral chamfer cut 62, posterior femoral chamfer cut 64, and posterior femoral cut 66. For complete knee replacement procedures, patella cut 68 may also be made to allow for replacement of the patellar articular surface. In a unicondylar knee replacement, only the medial or lateral side of the knee joint is resurfaced. Furthermore, the trochlear, or patellar bearing, surface of the femur is typically left intact in a unicondylar procedure. Unicondylar implant designs vary, but typically only distal femoral cut 50, posterior femoral chamfer cut 64, and posterior femoral cut 66 are needed (for either the lateral or medial femoral condyle) to accommodate the unicondylar femoral implant.

Turning back to FIG. 3B, femoral component 100 is adapted to mount to the resulting five-faceted distal femoral bone surface. Femoral component includes posterior facet 140, posterior chamfer 142, distal facet 144, anterior chamfer 146, and anterior facet 148 which mate with cuts 66, 64, 50, 62, 60 respectively. As noted above, the surgical technique for implanting component 100 will typically specify that distal cut 50 be perpendicular to mechanical axis MA of femur F, meaning distal facet 144 will also be perpendicular to mechanical axis MA after implantation.

Where distal facet 144 is so configured, distal-most points 132, 134 may be considered to be the points on femoral condyles 114, 115 which are furthest from distal facet 144 (i.e., at the "thickest" parts of the material of distal portion of condyles 114, 115). Similarly, in some cases coronal plane CP may be tangent to the femoral articular surface at the posterior-most point of lateral femoral condyle 114, where the posterior-most points are those points on the articular surface furthest from posterior facet 140. Posterior facet 140 and distal facet 144 are frequently perpendicular to one another in femoral prosthetic components, such that distal facet 144 and posterior facet 140 may also be parallel to transverse plane TP and coronal plane CP, respectively.

Similarly, sagittal plane SP may be defined in other ways, depending on the particular geometry of a femoral component. For example, femoral component 100 is a "posterior stabilized" or PS design, which includes intercondylar notch 150 (FIG. 3A) designed to articulate with a tibial spine or eminence 152 of tibial component 122 (FIG. 2C). In a PS design, it may sometimes be appropriate to define sagittal plane SP as a plane which is equidistant from the medial and lateral intercondylar walls 154, 156 (FIG. 3A) of intercondylar notch 150. In some other embodiments, sagittal plane SP may be equidistant from the medial edge 158 of medial condyle 115 and lateral edge 160 of lateral condyle 114.

Moreover, it is contemplated that any number of knee prosthesis designs may be modified to include lateral condylar divergence in accordance with the present disclosure, and that coordinate planes SP, TP, CP may shift slightly depending on a particular design.

Figure 3C:
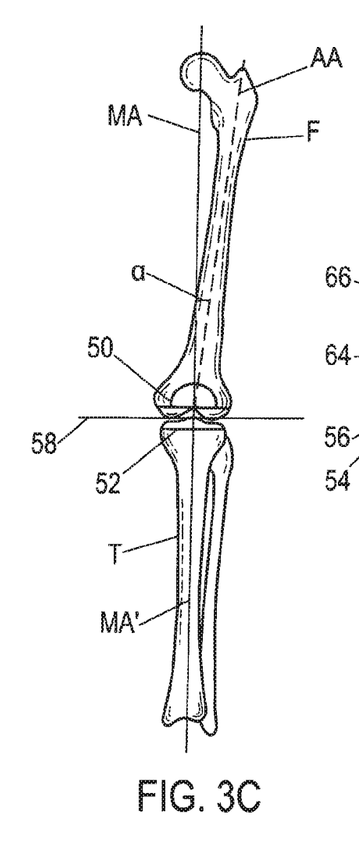
FIG. 3C is a coronal, elevation view of a femur, illustrating anatomical and mechanical axes thereof.
Figure 3D:
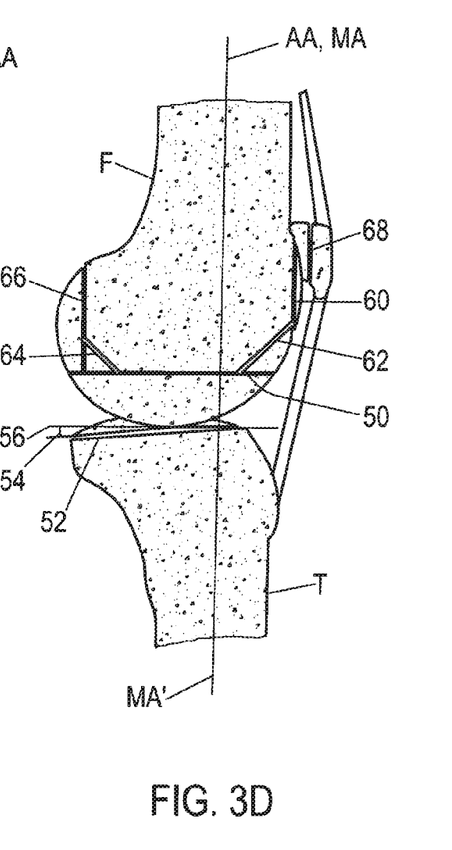
FIG. 3D is a sagittal, elevation view of a knee joint, illustrating resections for prosthesis implantation.

For example, some femoral components may be designed for femoral resections which are indexed to anatomical axis AA (FIG. 3C). FIG. 3C illustrates femur F as shown from a frontal (i.e., coronal) view. Femur F defines anatomic axis AA coinciding generally with the axis of the natural intramedullary canal of femur F. Femur F also has mechanical axis MA, sometimes referred to as the "load axis" because mechanical axis MA runs from the center of the load-bearing femoral head to the center of the load-bearing articular surfaces of the knee. Angle α is formed between axes MA, AA in the coronal plane. Angle α varies within the patient population, but is on the order of 4-9°. As noted above and shown in FIG. 3D, axes MA, AA are approximately superimposed when viewed from a sagittal perspective. Tibia T has mechanical axis MA' coinciding generally with the intramedullary canal of tibia T. Mechanical axis MA' of tibia T runs from the center of the knee to the center of the ankle.

Examples of femoral components whose implantation is indexed to the anatomic axis (i.e., axis AA) are disclosed in U.S. Provisional Patent Application Ser. No. 61/381,803 filed Sep. 10, 2010 and entitled "Femoral Prosthesis With Medialized Patella Groove", the entire disclosure of which is hereby expressly incorporated by reference herein. Such designs may have a changed geometrical arrangement of the distal facet (analogous to distal facet 144 of femoral component 100), and the articulation axis (analogous to axis 138 of femoral component 100) with respect to the distal-most points of the femoral condyles. In other designs, the distal facet of a femoral component may not be planar, or may not be perpendicular to either mechanical axis MA or anatomical axis AA. For these and other geometrically varied components, a distal facet may not be a suitable point of reference for defining distal-most points. Instead, the points of contact between femoral condyles and a tibial bearing component may be used as described in detail above.

However a particular prosthetic component is constructed, one having ordinary skill in the art of orthopaedic prostheses will be able to choose a method for defining appropriate component coordinate planes within the spirit and scope of the present disclosure. For example, although a given prosthesis design may not have "distal-most points" amenable to the exemplary definitions used herein, one of ordinary skill in the present art will recognize that "distal most points" are those points on the component which correspond to the portions of natural femoral condyles that contact the proximal tibia when a healthy, natural knee is in full extension.

Characteristics of the Femoral Component During Use

As noted above, femoral component 100 defines laterally divergent condylar spacing which, as shown in FIG. 2C, cooperates with tibial component 122 to provide a substantially linear lateral articulation path 130 between lateral condyle 114 and lateral tibial articular surface 126 during articulation from extension to flexion.

Turning to FIG. 4, it can be seen that condylar spacing CS 1 is defined between lateral and medial distal-most points 132, 134, respectively. Moving posteriorly along the convex articular surfaces of lateral and medial femoral condyles 114, 115, lateral and medial contact points 162, 164 correspond with a 45° flexion orientation of femoral component 100. Going further into flexion, lateral and medial contact points 166, 168 correspond with 90° flexion, while lateral and medial contact points 170, 172 correspond with 135° flexion. Each of the above-mentioned contact points rest upon tibial component 122 at various levels of flexion, as described below.

In the illustrated embodiment, medial tibial articular surface 124 is highly congruent with medial femoral condyle 115 throughout the flexion range, such that medial femoral condyle 115 contacts medial tibial articulation surface 124 at a single spatial position disposed on tibial articulation surface 124 throughout the range of articulation. More particularly, this high congruence results in a requirement of substantial force to advance any of medial femoral contact points 134, 164, 168, 172 anteriorly or posteriorly away from medial contact point 128 of medial tibial articular surface 124 at respective levels of articulation.

Meanwhile, the congruence between lateral tibial articular surface 126 and lateral condyle 114 is somewhat lower, such that a lower force threshold is required to slide contact points 132, 162, 166, 170 of lateral condyle 114 with respect to lateral tibial articular surface 126 during articulation. Thus, the natural articular forces generated to promote femoral rollback during articulation may cause lateral condyle 114 to slide or "roll back" along lateral linear path 130 during articulation from extension to deep flexion, as described in detail below. Interaction between spine 152 (FIG. 2C) and femoral cam 153 (FIG. 4) may also induce femoral rollback in deep flexion.

Figure 5A:
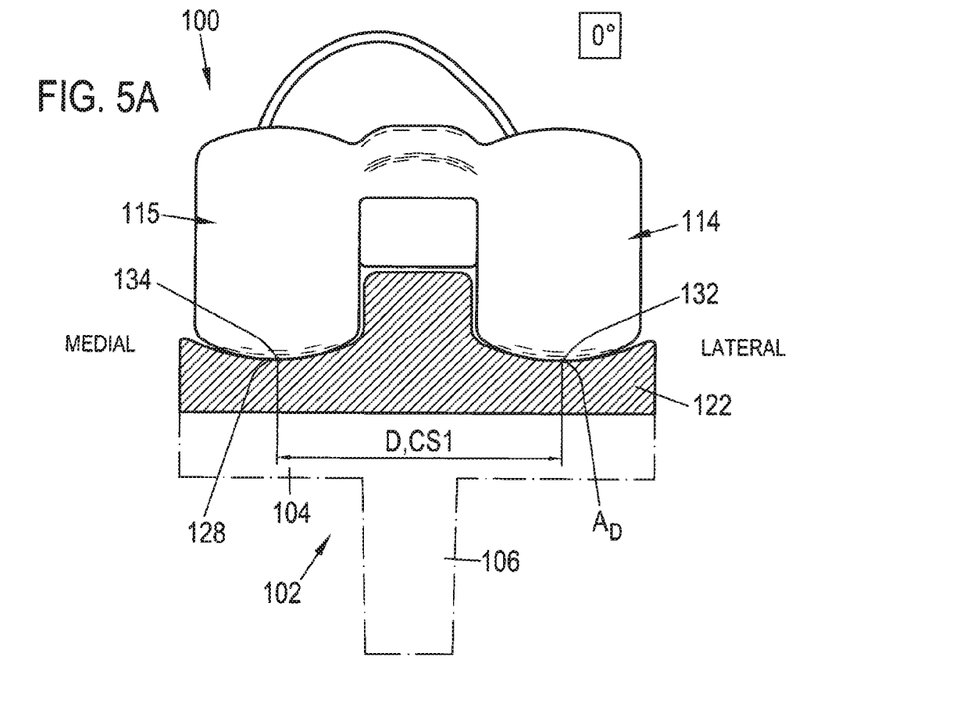
FIG. 5A is a coronal, elevation view of the femoral component shown in FIG. 3A, in which the femoral component is shown resting upon a tibial component in an extension configuration.

As shown in FIG. 5A, when femoral component 100 is seated on tibial component 122 in a fully-extended orientation (i.e., 0° flexion), distal-most point 132 is seated at contact point $A_D$ on lateral tibial articular surface 126. Similarly, distal-most point 134 of medial condyle 115 is seated upon medial contact point 128 of medial tibial articular surface 124. Distance D, which is parallel to coronal plane CP, is defined between contact points 128, $A_D$. In the extension orientation, distance D is equal to condylar spacing CS1 (FIG. 4). For purposes of the discussion below, distance D is considered to be a distance projected in coronal plane CP, as illustrated in FIGS. 5A-5D.

For purposes of illustration, FIG. 5A shows tibial component 122 seated upon tibial baseplate 102, which includes a proximal base platform 104 and a stem or keel 106 extending distally from platform 104. Base platform 104 has a proximal surface sized to receive the distal surface of tibial component 122, while keel 106 is received within the intramedullary canal of a tibia upon implantation. For simplicity, tibial baseplate 102 is excluded from FIGS. 5B-5D, though it is to be understood that a complete knee prosthesis will typically include baseplate 102.

Figure 5B:
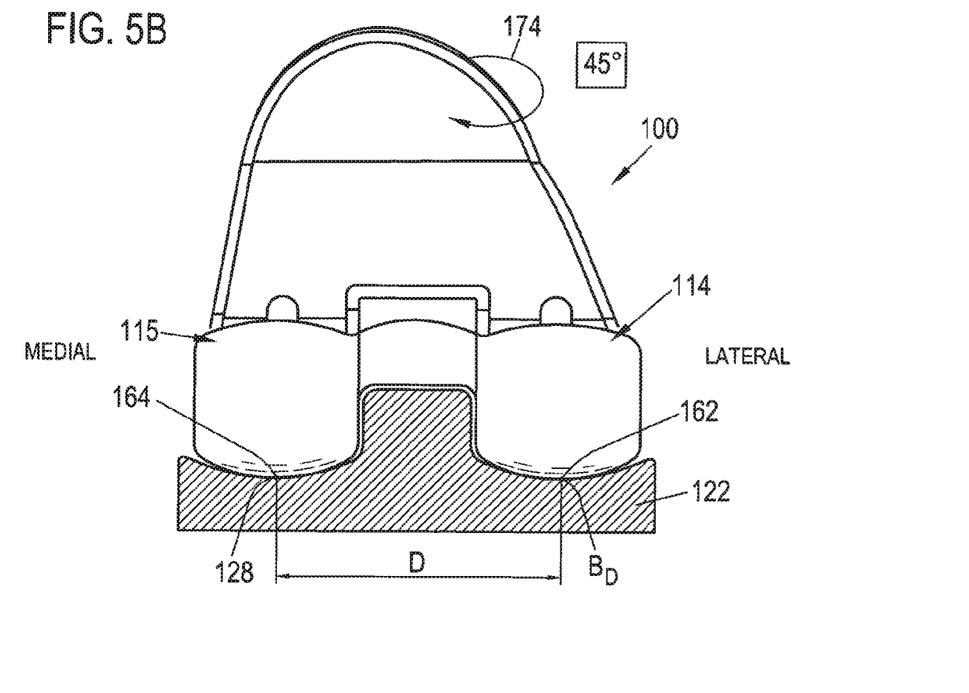
FIG. 5B is another elevation view of the femoral and tibial components shown in FIG. 5A, in which the femoral component has been articulated to a 45° flexion configuration.

Turning now to FIG. 5B, femoral component 100 is shown in a 45° flexion orientation. In the process of flexing from 0° to 45° flexion, femoral component 100 has externally rotated along rotation direction 174. In so rotating, femoral component 100 has pivoted about medial contact point 128. This pivot point is created by the high geometrical congruence between medial condyle 115 and medial articular surface 124, discussed above Thus, both medial distal-most contact point 134 and medial 45°-contact point 164 coincide with medial contact point 128 on medial tibial articular surface 124, while lateral 45°-contact point has been allowed to roll back as femoral component 100 externally rotates during flexion. As this lateral femoral rollback occurs, condylar spacing increases (from CS 1 in extension to CS2 in flexion). The increase in condylar spacing offsets the inward curving of linear path 130 which would otherwise occur (see, for example, arcuate path 30 in FIG. 1C), thereby maintaining the same distance D (as projected in coronal plane CP) between medial contact point 128 and contact point $B_D$ as was present in full extension (discussed above). More particularly, the extra space provided in condylar spacing CS2 may be specifically calculated to compensate for expected posterior travel of lateral condyle 114 due to femoral rollback, which in turn allows the portion of lateral path 130 between contact points $A_D$ and $B_D$ (FIG. 2C) to be linear and anteroposteriorly oriented.

Figure 5C:
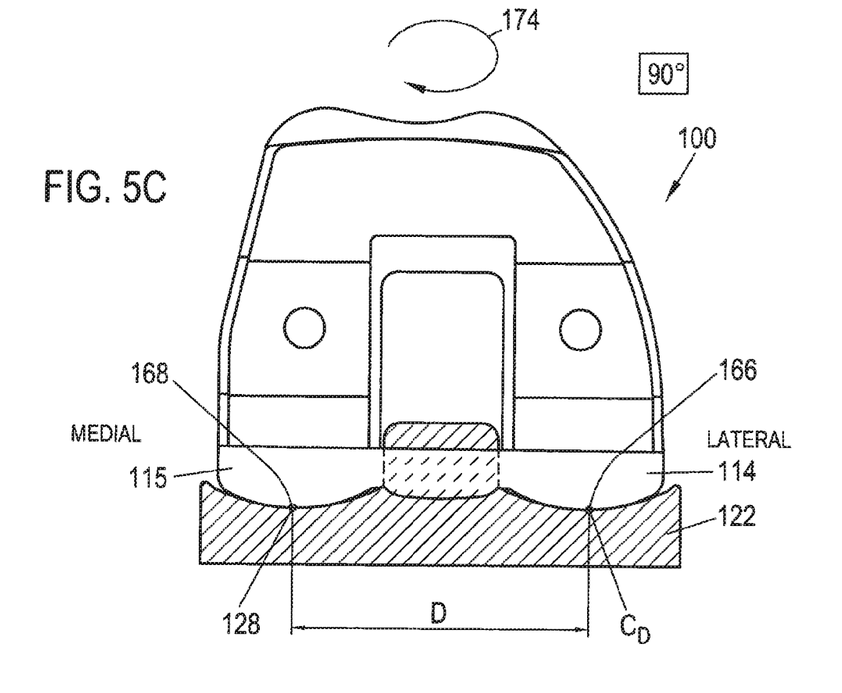
FIG. 5C is another elevation view of the femoral and tibial components shown in FIG. 5A, in which the femoral component has been articulated to a 90° flexion configuration.

Turning now to FIG. 5C, femoral component 100 is shown in after having articulated to 90° flexion with respect to tibial component 122. Lateral 90°-contact point 166 now contacts lateral tibial articular surface 126 at contact point $C_D$, while medial 90°-contact point 168 remains centered upon medial contact point 128 of medial tibial articular surface 124. As illustrated in FIGS. 2B, 2C and 4, condylar spacing CS3 between lateral and medial 45° contact points 166, 168 is larger than condylar spacings CS1 and CS2. However, femoral component 100 has continued to externally rotate about rotation direction 174, which in turn maintains distance D (as projected in coronal plane CP) between medial contact point 128 and lateral 90° contact point $C_D$. As above, keeping distance D consistent despite the external rotation of femoral component 100 is accomplished by the increase in condylar spacing exemplified by CS3 compensating for the posterior rollback of lateral femoral condyle 114, as shown schematically in FIG. 2C.

Figure 5D:
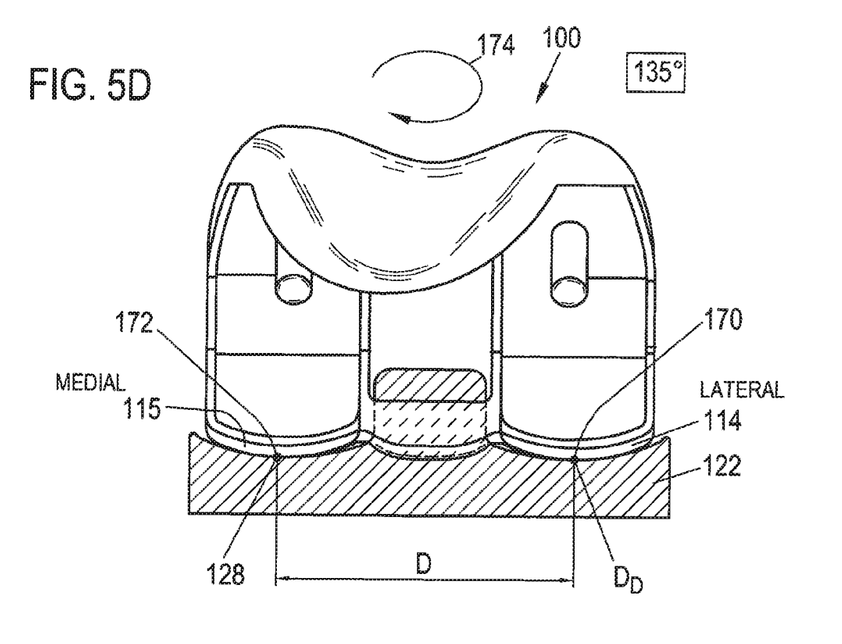
FIG. 5D is another elevation view of the femoral and tibial components shown in FIG. 5A, in which the femoral component has been articulated to a 135° flexion configuration.

FIG. 5D shows femoral component 100 in a deep flexion orientation, such as 135° flexion. As shown in FIGS. 2B, 2C and 4, lateral and medial contact points 170, 172 define condylar spacing CS4 which is larger than all of condylar spacings CS1, CS2 and CS3. However, as above, medial 135°-contact point remains centered at medial contact point 128, which is located distance D from lateral contact point $D_D$ and lateral 135°-contact point 170. As above, the amount of divergence of lateral condyle 114 is calculated to compensate for external rotation along rotation direction 174 (as schematically illustrated in FIG. 2C).

As noted above, femoral rollback is a phenomenon that occurs in the natural knee and is replicated in many prosthetic knee designs. It is appreciated that femoral rollback may be accomplished by a number of prosthesis mechanisms and/or component geometries. Differential congruence between the lateral and medial articular surfaces of a knee prosthesis, as described in detail above, is one such mechanism. Cam/spine interaction in posterior-stabilized prostheses is another mechanism. Still other mechanisms may be employed. Regardless of the motive force for femoral rollback, divergence of lateral femoral condyle 114 is operable to facilitate the lateral linear path 130 followed by lateral contact points 132, 162, 166, and 170 during articulation. The magnitude and profile of such divergence can be modified to match the particular external rotation/femoral rollback profile for a given prosthesis design.

Advantageously, as shown in FIG. 2C, divergent lateral femoral condyle 114 operates to maintain linear path 130 which matches a straight anteroposterior depression 176 in lateral tibial articular surface 126. In doing so, the large-area contact between lateral tibial articulation surface 126 and lateral femoral condyle 114 present at extension (see the contact around contact point $A_D$ in FIG. 5A) is maintained throughout flexion (see the corresponding large-area contact around contact points $B_D$, $C_D$, $D_D$ in FIGS. 5B, 5C, and 5D respectively). On the other hand, arcuate path 30 arising from constant bearing spacing CS (FIG. 1C) would feature a decreasing contact area when paired with a straight lateral articular depression, because lateral condyle 14 would not remain centered at the bottom of the convex face defined by lateral articular surface 26.

While the prosthesis design shown and described above is a "complete" knee replacement, it is contemplated that partial knee replacements may also be made in accordance with the present disclosure. For example, a lateral unicondylar knee replacement may feature divergent condylar spacing with respect to the natural medial condyle, which in turn may enjoy the benefits described above.

While this disclosure has been described as having exemplary designs, the present disclosure can be further modified within the spirit and scope of this disclosure. This application is therefore intended to cover any variations, uses, or adaptations of the disclosure using its general principles. Further, this application is intended to cover such departures from the present disclosure as come within known or customary practice in the art to which this disclosure pertains and which fall within the limits of the appended claims.

What is claimed is:

1. A femoral component for a knee prosthesis, the femoral component comprising:
   a medial condyle having a convex medial articular surface defining:
      a medial distal-most point, and an arcuate medial condylar track extending posteriorly along said medial articular surface from said medial distal-most point, said arcuate medial condylar track defining a medial radius of articulation; and
   a lateral condyle having a convex lateral articular surface defining:
      a lateral distal-most point, and an arcuate lateral condylar track extending posteriorly along said lateral articular surface from said lateral distal-most point, said arcuate lateral condylar track defining a lateral radius of articulation, said femoral component defining:
         an articulation axis passing through said medial radius of articulation and said lateral radius of articulation, a transverse plane tangent to at least one of said lateral distal-most point and said medial distal-most point, a coronal plane perpendicular to said transverse plane, parallel to said articulation axis, and tangent to at least one of said medial articular surface and said lateral articular surface, and a sagittal plane perpendicular to said transverse plane and said coronal plane, said sagittal plane mediolaterally positioned to bisect said articulation axis, said arcuate medial condylar track defining a constant condylar spacing from said sagittal plane, and said arcuate lateral condylar track defining a divergent condylar spacing from said sagittal plane as said lateral condylar track extends posteriorly.

2. The femoral component of claim 1, in combination with:
   a tibial bearing component defining:
      a medial articular surface shaped and positioned to articulate with said medial condyle of said femoral component, said medial articular surface forming a pivot point for external rotation of said femoral component during a flexion articulation with said tibial bearing component;
   a lateral articular surface shaped and positioned to articulate with said lateral condyle of said femoral component, such that said lateral condyle rolls back on said lateral articular surface during said external rotation to define an articulation path, said divergent condylar spacing calculated to compensate for said external rotation such that said articulation path is anteroposteriorly oriented and linear.

3. The combination of claim 2, wherein:
   said medial articular surface defines a relatively higher congruence with said medial condyle of said femoral component, whereby said medial condyle is constrained to a pivoting motion about said pivot point during articulation, and said lateral articular surface defines a relatively lower congruence with said lateral condyle of said femoral component, whereby said lateral condyle is permitted to roll back on said lateral articular surface along said linear articulation path.

4. The combination of claim 2, wherein said medial distal-most point is defined as a point of contact between said medial condyle and said medial articular surface when said femoral component is in a full-extension orientation with respect to said tibial bearing component.

5. The combination of claim 2, wherein said lateral distal-most point is defined as a point of contact between said lateral condyle and said lateral articular surface when said femoral component is in a full-extension orientation with respect to said tibial bearing component.

6. The femoral component of claim 1, wherein said femoral component is adapted to mount to a distal cut on a femur, in which the distal cut is normal to a mechanical axis of the femur, the femoral component comprising:
   a medial distal facet sized and adapted to mount to the distal cut on the femur, in which said medial distal-most point is the point at which material of said medial condyle is thickest with respect to said medial distal facet.

7. The femoral component of claim 1, wherein said femoral component is adapted to mount to a distal cut on a femur, in which the distal cut is normal to a mechanical axis of the femur, the femoral component comprising:
   a lateral distal facet sized and adapted to mount to the distal cut on the femur, in which said lateral distal-most point is the point at which material of said lateral condyle is thickest with respect to said lateral distal facet.

8. A knee prosthesis comprising:
   a femoral component having a convex medial femoral condyle and a convex lateral femoral condyle; and
   a tibial bearing component having a medial articular surface adapted to articulate with said medial femoral condyle through a range of flexion, and a lateral articular surface adapted to articulate with said lateral femoral condyle through the range of flexion, said medial femoral condyle defining a plurality of medial femoral contact points with said medial articular surface at a plurality of flexion levels within the range of flexion, each of said medial femoral contact points disposed at a substantially constant spatial position on said medial articular surface, said lateral femoral condyle defining a plurality of lateral femoral contact points with said lateral articular surface at the plurality of flexion levels, each of said lateral femoral contact points disposed along a substantially linear path on said lateral articular surface.

9. The knee prosthesis of claim 8, wherein said femoral component defines an external rotation with respect to said tibial bearing component during articulation, said external rotation occurring about a pivot located at said constant spatial position.

10. The knee prosthesis of claim 9, wherein said lateral condyle rolls back on said lateral articular surface during said external rotation to define said substantially linear path.

11. The knee prosthesis of claim 9, wherein said lateral condyle of said femoral component defines divergent condylar spacing calculated to compensate for said external rotation such that said substantially linear path is anteroposteriorly oriented.

12. The knee prosthesis of claim 8, wherein said femoral component defines:
   a transverse plane tangent to at least one of a lateral distal-most point formed on said lateral condyle and a medial distal-most point formed on said medial condyle;
   a coronal plane that is perpendicular to said transverse plane, parallel to a line drawn between said medial distal-most point and said lateral distal-most point, and tangent to a posterior convex surface formed on at least one of said medial articular surface and said lateral articular surface; and a sagittal plane perpendicular to said transverse plane and said coronal plane, said sagittal plane mediolaterally positioned to bisect said line drawn between said medial distal-most point and said lateral distal-most point, said plurality of medial femoral contact points each having equal spacing from said sagittal plane, and said plurality of lateral femoral contact points having increasing spacing from said sagittal plane as said femoral component is articulated through the range of flexion starting from an extension configuration of the knee prosthesis.

13. A knee prosthesis comprising:

a femoral component having a convex medial femoral condyle and a convex lateral femoral condyle; and a tibial bearing component having a medial articular surface adapted to articulate with said medial femoral condyle through a range of flexion, and a lateral articular surface adapted to articulate with said lateral femoral condyle through the range of flexion, said medial femoral condyle contacting a medial point on said medial articular surface at a first degree of flexion, said medial femoral condyle maintaining contact with said medial point at a second degree of flexion, said lateral femoral condyle contacting a lateral point on said lateral articular surface at the first degree of flexion, said lateral femoral condyle losing contact with said lateral point at the second degree of flexion, said lateral femoral condyle experiencing rollback along a substantially linear path from said first degree of flexion to said second degree of flexion.

* * * * *